United States Patent [19]

Flider et al.

[11] 4,399,224

[45] Aug. 16, 1983

[54] ENZYMATICALLY TREATED PHOSPHATIDES

[75] Inventors: Frank J. Flider, Mt. Zion; Frank T. Orthoefer; Robert G. Short, both of Decatur, all of Ill.

[73] Assignee: A. E. Staley Manufacturing Company, Decatur, Ill.

[21] Appl. No.: 282,557

[22] Filed: Jul. 13, 1981

[51] Int. Cl.$^3$ .......................... C11C 1/00; A23J 7/00
[52] U.S. Cl. ...................................... 435/271; 426/7; 426/662
[58] Field of Search ................... 435/267, 271, 134, 7; 426/46, 662

[56] References Cited

U.S. PATENT DOCUMENTS

| | | | |
|---|---|---|---|
| 2,194,842 | 3/1940 | Wiesehahn | 252/1 |
| 2,351,184 | 6/1944 | Boone | 260/424 |
| 2,374,681 | 5/1945 | Julian et al. | 252/1 |
| 2,391,462 | 12/1945 | Julian et al. | 252/1 |
| 2,483,748 | 10/1949 | Wittcoff | 252/1 |
| 2,494,771 | 1/1950 | Markley | 99/18 |
| 2,555,137 | 5/1951 | Karjala | 252/1 |
| 2,576,958 | 12/1951 | Mattikow | 260/426 |
| 2,666,074 | 1/1954 | Sadler | 260/424 |
| 2,696,190 | 8/1954 | Myers | 260/403 |
| 2,983,612 | 5/1961 | Eichberg | 435/27 X |
| 3,357,918 | 12/1967 | Davis | 252/1 |
| 3,878,232 | 4/1975 | Hayes et al. | 260/412.4 |
| 4,119,564 | 10/1978 | Van Dorn | 252/312 |
| 4,141,792 | 2/1979 | Hayash | 195/99 |
| 4,162,260 | 7/1979 | Segers | 260/424 |

FOREIGN PATENT DOCUMENTS 1053807 1/1967 United Kingdom .

OTHER PUBLICATIONS

Kirk–Othmer Encyclopedia of Chemical Technology, 2nd Edition, vol. 12, p. 347.
Enzyme Nomenclature Recommendations–International Union of Pure and Applied Chemistry & International Union of Biochemistry (1972), pp. 212–218.

Primary Examiner—Lionel M. Shapiro
Attorney, Agent, or Firm—M. Paul Hendrickson; Charles J. Meyerson

[57] ABSTRACT

It has been discovered that phosphatides contain certain carbohydrates which adversely affect their functional properties. By hydrolyzing such carbohydrates with an effective amount of carbohydrase, the physical and functional properties of such phosphatides are significantly improved. In the manufacture of lecithin, wet gums enzymatically treated with carbohydrases dehydrate more rapidly into a low moisture lecithin product. The enzymatic treatment also fluidizes phosphatide compositions and stabilizes the compositions against solidification.

10 Claims, No Drawings

ENZYMATICALLY TREATED PHOSPHATIDES

BACKGROUND OF THE INVENTION

Phosphatides occur widely in vegetable and animal matter, but soybeans are the principal commercial source. In the refining of crude vegetable oils, it is conventional to remove phosphatides (frequently referred to as lecithin) from the oil. This process is commonly referred to as "degumming". Degumming is typically achieved by hydrating the lecithin-containing crude oil and recovering the insoluble hydrated lecithin (frequently referred to as "wet gum") from the oil. A commercial lecithin product is then obtained by drying the wet gum. The lecithin of commerce ordinarily contains about one-third oil and about two-thirds phosphatides. Such commercial lecithin products generally have an acetone insoluble (A.I.) of at least 50 and are most typically within about the 60 to about 65 A.I. range. In the trade, 65% A.I. commercial lecithin is a familiar commodity.

The difficulties encountered with commercial vegetable lecithin are due to its viscosity characteristics and a tendency to settle and form layers upon storage. Such lecithins are fairly viscous when first prepared, but subsequently solidify or develop a heavy layer which separates from a lighter oily layer. This tendency to solidify or settle into a hard lower layer and an oily top layer is accentuated under cold storage conditions.

Considerable inconvenience, loss and waste of lecithin also arises through the commercial use of high viscosity lecithins. The high viscosity lecithins tend to stick to equipment and containers which make it difficult to accurately weight, transfer and expeditiously use the lecithin product in recipes formulated therewith.

The art has sought to overcome the aforementioned shortcomings by numerous different approaches. It has been recognized that the low viscosity 65 A.I. lecithins are less prone to separate and form a plastic mass and can be more easily handled. A common practice is to introduce fluidization agents to control the fluidity or viscosity of the lecithin. One approach is to use a diluent such as an oil or solvent adjunct to fluidize the lecithin mixture. Such an approach has the disadvantage of reducing the A.I. value while introducing non-functional and undesirable diluents into the lecithin product. Numerous other patents suggest that lecithin may be fluidized with a wide variety of acids (e.g. U.S. Pat. Nos. 2,194,842—fatty acids; 2,374,681—sulfonic acid; 2,391,462—aqueous acid; 2,483,748—fatty acid esters; 2,494,771—aliphatic acid; 2,555,137—lactic acid, etc.) in varying amounts. U.S. Pat. No. 2,686,190 reports that lecithin can be converted to a more fluid form without requiring the presence of fluidization agents by reducing the water content of the wet gum to not more than about 0.3% by weight water. Another U.S. Pat. No. (3,357,918) indicates that certain salts of magnesium, calcium and aluminum impart fluidity to lecithin in specified amounts.

Numerous other patents (e.g. see U.S. Pat. Nos. 3,878,232; 4,162,260; 2,351,184; 2,576,958 and 2,666,074, French Pat. Nos. 1,388,671 and 1,385,670 and British Pat. No. 1,053,807) physically separate or fractionate certain components from lecithin-containing oils to provide a refined oil product which, in some instances, reportedly improves upon the quality of lecithin.

Enzymatic treatments which alter phospholipid structure have been reported. U.S. Pat. No. 4,119,564 reports the treatment of phospholipoproteins with phospholipase A (snake venom) to increase the viscosity imparting properties of the lecithin in oil-in-water emulsions. Similarly U.S. Pat. No. 4,141,792 reports the quantitative analysis of phospholipids content by enzymatically treating test samples with certain phospholipases. Lecithin has also been treated with enzymes which split off the fatty acid radicals (e.g. esterases—Kirk-Othmer Encyclopedia of Chemical Technology, 2nd Ed., Volume 12, page 349).

As evident from the above, two saliently different approaches have been taken to improve 65 A.I. lecithin products. One approach involves physical purification to remove certain impurities from the lecithin-containing oil-base stock while the other approach relies upon the addition of fluidization agents. The first approach typically involves substantial capital expenditures, costly and tedious processing controls, etc., for improvements, which in many instances, do not significantly improve or correct the aforementioned lecithin deficiencies. Similarly the addition of fluidization agents does not afford a satisfactory solution. Lecithin products are known to vary considerably from one manufacturing lot to another. The character and nature of soybean raw materials (which vary considerably due to variety, climate, maturity, etc.), the processing and manufacturing conditions and other related matters make it difficult to accurately control or regulate the precise amount of fluidization agents needed to achieve the desired affect in any given manufacturing lot. Moreover, such additives often destroy or mask other desirable functional or physical attributes of the native lecithin product. Due to a wide variety of industrial, pharmaceutical, agricultural and food applications, such additives often become incompatible with the recipe components and its intended end-use.

Notwithstanding a long-felt need to improve upon these deficiencies, the prior art has made relatively minor progress in improving upon lecithin manufacture. A simplified, cost-effective 65 A.I. lecithin manufacturing process which would not contaminate or destroy the indigenous characteristics of lecithin would be of substantial benefit. The inventors discovered that the problems, which have heretofore plagued the prior art, can be effectively overcome by hydrolyzing the polysaccharide component of lecithin-containing oil-based stocks or other lecithin-containing compositions with carbohydrases. Through the conversion of these polysaccharides into hydrolyzates, fluid lecithins which remain stable over prolonged storage periods under diverse climatic conditions without requiring supplemental additives are now feasible.

DESCRIPTION OF THE INVENTION

According to the present invention there is provided a method for converting phosphatide compositions which contain indigenous polysaccharide components to fluid phosphatide compositions, said method comprising treating the phosphatide composition with an effective amount of carbohydrase to hydrolyze the polysaccharide component and thereby improve upon the fluidity characteristics of said phosphatide composition, and recovering the fluid phosphatide composition.

Phosphatides derived from vegetative sources contain O-glycosyl compounds such as di-, tri- and tetrasaccharide sugars (e.g. stachyose, raffinose, sucrose, etc.), sterol glucosides, isoflavone glucosides, saponins, etc.

The crude oil obtained from the defatting of vegetable material will contain O-glycosyl compounds as well as the phosphatides and oil extract. Certain of the O-glycosyl compounds apparently complex with the phosphatides and will remain with the phosphatides after the crude oil degumming step. It now appears as though these O-glycosyl compounds adversely affect the physical and functional properties of phosphatides.

By hydrolyzing these O-glycosyl compounds with a glucosidase, it is now feasible to produce a low viscosity and stable phosphatide composition. The enzymatic phosphatide treatment avoids the need to use fluidization agents. Unlike acid fluidization agents, which also hydrolyze phosphatides, the enzymatic activity of the glucosidase is specific in its hydrolysis of O-glycosyl compounds. Thus, the O-glycosyl compounds are selectively hydrolyzed into a non-complexing form without causing hydrolysis of the phosphatide. *Enzyme Nomenclature Recommendations* (1972) of the International Union of Pure and Applied Chemistry and International Union of Biochemistry classifies glucosidases and hydrolases under "3.2 ACTING ON GLYCOSYL COMPOUNDS." Glucosidases which hydrolyze O-glycosyl compounds are further identified by the 2.3.1 numerical designation. Exemplary O-glycosyl glucosidases include the 3.2.1.20 alpha-glucosidase which hydrolyze the terminal non-reducing 1,4,-alpha-D-glucose residue to alpha-glucose (e.g. glucoinvertase, glucosidosucrase, alpha-D-glucoside glucohydrolase); 3.2.1.22 alpha-D-galactoside galactohydrolase (which hydrolyze terminal non-reducing alpha-D-galactose residues in alpha-galactoside such as galactose oligosaccharides, galactomannans) and alpha-D-galactohydrolase (e.g. melibiase), etc; 3.2.1.26 beta-fructofuranosidase (which hydrolyzes the terminal non-reducing beta-D-fructofuranoside residues in beta-fructofuranosides) such as sucrase, invertase, invertin, saccharase and beta-fructosidase; 3.2.1.48, sucrase-alpha-glucohydrolase which hydrolyzes sucrose and maltose by an alpha-glucosidase-type action (more commonly known as sucrose-alpha-glucohydrolase), mixtures thereof and the like.

The enzymatic treatment of the phosphatide may occur at any stage of the lecithin manufacture, and especially when water is incorporated or utilized in the phosphatide manufacture.

In the manufacture of lecithin, the degumming aqueous phase provides a particularly appropriate substrate for hydrolyzing the O-glycosyl compounds. Degumming involves the addition of water to hydrate the phosphatide. The hydrated and oil-immiscible lecithin will migrate to the aqueous phase. The hydrated lecithin may then be easily separated from the oil phase. By adjusting the pH of the hydrated wet gum (e.g. after its separation) to the appropriate pH level for enzymatic treatment, the hydrolysis of the O-glycosyl compound within the phosphatide composition may be effectuated. The optimum hydrolyzing pH will depend upon the particular glucosidase chosen to hydrolyze the O-glycosyl compounds. This can vary considerably between different types of glucosidases, but will most generally fall within the pH 4.5–8.5 range. The optimum pH and temperature ranges for any particular glucosidase may also be obtained from the literature and trade publications. The beta-fructofuranosidases (beta-fructofuranoside, fructohydrolase—3.2.1.26) are a particularly effective glucosidase. It has an optimum stability within the pH 4.5–6.5 range and an optimum activity within the pH 4.5–5 range.

The enzymatic treatment of this invention may also be applied to improve upon the fluidity and stability of dry phosphatides. The dry phosphatide compositions are rehydrated with a sufficient amount of water to permit the glucosidase to hydrolyze the O-glycosyl components.

For most operations, the weight ratio of the water to dry phosphatide will depend upon the particular requirements of the hydrolyzing enzyme. The amount of water should be sufficient to permit the enzyme or enzyme system to hydrolyze the O-glycosyl compounds. Although this may vary considerably (e.g. about 1:20 to about 20:1), it is most practical to operate at about 3:1 to about 1:3 (preferably from about 2:1 to about 1:2) water to dry phosphatide weight ratio.

The hydrolyzing temperature and glucosidase units required to fluidize the phosphatide will depend upon the enzymatic activity characteristics of the particular enzyme used to hydrolyze the phosphatide composition. This may vary from one enzyme to another. In general, the hydrolysis will be conducted between 10°–90° C. with temperatures ranging from about 15° C. to about 40° C. being most typical. The hydrolyzing period likewise depends upon the pH, temperature and glucosidase hydrolyzing activity. For most commercial operations, the hydrolysis can be completed within a time interval ranging from about 1 minute to several hours and most typically between about 5 minutes to about 8 hours. Longer digestive periods are not required, but may be suitably adapted to conform with the normal time interval required to commercially process a wet gum.

The enzymatic treatment beneficially affects the processability of the phosphatide composition. It appears as though the digestion disrupts carbohydrate/phosphatide complexes and results in the release of entrapped and tenaciously held water. Thus, the treated wet gums easily dehydrate into a high quality, fluid phosphatide product.

The enzymatic treatment of glucosidic compounds hydrolyzes the polysaccharides (i.e. di- and higher) into monosaccharides which improves upon the viscosity and stability attributes of the phosphatide composition. Highly viscous, sticky and plastic wet gums or dehydrated lecithins can be easily converted into a fluid product. Unlike the high viscosity wet gums or lecithins which tend to stick to processing equipment and tenaciously retain water, the fluidized products produced under the subject invention can be easily handled and processed with conventional equipment.

It is often advantageous to include an additional enzyme along with the glucosidase for the purpose of enabling the glucosidase to more completely hydrolyze the O-glycosyl compounds to monosaccharides. Certain glucosidases are unable to completely convert all of the O-glycosyl di- and higher saccharides into the desired monosaccharide hydrolyzate product. Glucosidases which hydrolyze O-glycosyl compounds to monosaccharides normally have the capacity to repolymerize monosaccharides into polysaccharides. By removing or converting the monosaccharide hydrolyzates during the hydrolysis, the enzymatic equilibrium can be shifted to permit more complete conversion of the O-glycosyl composition to monosaccharides. Such supplemental enzymes increase the amount of O-glycosyl compounds which may be hydrolyzed by the glucosidase to monosaccharides. For example, when invertase is used to enzymatically treat the phosphatide composition, the invertase hydrolyzes the sucrose to glucose and fructose, the raffinose to melibiose and fructose and stachyose to mannotriose and fructose. By including glucose oxidase in the enzymatic treatment process, the glucose is converted to gluconic acid and hydrogen peroxide which enables the invertase to more completely hydrolyze the polysaccharides to monosaccharides.

In addition to facilitating a more complete hydrolysis of the polysaccharides, the supplemental enzymes can also be effectively employed to improve upon the functional and physical properties of the phosphatide products. The ability of the glucose oxidase to convert the hydrolyzate products into hydrogen peroxide and gluconic acid results in several processing and product improvements. The enzymatically produced hydrogen peroxide functions as a bleaching agent to improve upon the phosphatide's flavor and color as well as functioning as an antiseptic or germicide. The gluconic acid improves upon the fluidity and thermal stability properties of the phosphatide. Other oxidases capable of converting the sugar hydrolyzate products into acids or peroxides (e.g. see Enzyme Nomenclature-oxidoreductases 1.1, acting on the CH-OH group of donors and especially 1.1.3 "with oxygen as acceptor") may also be used for this purpose. Similarly, supplemental enzymes capable of converting the sugar hydrolyzates into enzymatically produced flavor imparting agents may be combined with the carbohydrase to impart unique and desirable flavors to the processed phosphatide products.

In addition certain divalent metal ions, in small amounts, often improve upon the ability of the enzymes to hydrolyze the polysaccharides. Factors such as the divalent metal ion content and freeion concentration (e.g. ion uncomplexed or unbound to the phosphatide and available to the enzyme) of the undigested phosphatide substrate, the activating and stabilizing requirements of the enzyme, hydrolyzing temperature, pH conditions, etc. will affect the divalent metal ion requirements. As a general rule, the metal ion activators and stabilizers are most generally characterized as having a valance of two and an atomic number of 30 or less. The Period IIa metal ions (magnesium and calcium) and those metal ions of atomic numbers 22-30 inclusive (particularly manganous, ferrous and zinc), mixtures thereof and the like are most commonly used and reported as carbohydrase metal ion activators and/or stabilizers. Magnesium ion and to a lesser extent manganous, iron and zinc ions, have been used in combination with carbohydrase to facilitate the hydrolysis of saccharides. Calcium is often employed to stabilize the enzyme against thermal deactivation or denaturization.

Calcium and magnesium ions are indigenous metal ions of phosphatides, both of which can contribute to the divalent metal ion activity and stabilizing requirements of the enzyme. Under certain oil extracting conditions (e.g. azeotropic, alcohol/hexane extractions), the degummed dry phosphatide product often contains a lesser magnesium and calcium ion content than those normally obtained from hexane processed oils. Small amounts of a divalent metal ion (e.g. sufficient to provide 0.1% divalent metal ion concentration based upon a dry 65 A.I. weight basis) may be added to these phosphatides to facilitate their fluidization. Higher levels (e.g. 1% or higher) divalent metal ions may be used, but are not normally required for this purpose. Whether or not activating and stabilizing metal ions are needed for any given enzyme system and phosphatide product can be experimentally ascertained by observing the effects the divalent metal ions have upon fluidization of the phosphatide. For most operations, a phosphatide having a DVM content ranging from about 0.2% to about 0.6% (65 A.I. dry weight basis) will suffice.

The enzymatic treatment applies in general, to phosphatide compositions. Low A.I. lecithin products (e.g. 5–50 A.I.), which are most difficult to fluidize and maintain as a fluid may be enzymatically converted into shelf-stable, fluidized products. Caustic processed or partially hydrolyzed phosphatides may likewise be enzymatically treated to improve upon their functional properties.

The enzymatically treated phosphatide appears to possess unique compositional, functional and physical properties. The utility of conventional lecithin products is generally limited to those applications which do not exceed the thermal decomposition temperature of the lecithin. Excessive exposure to relatively low temperatures (e.g. 160° F.) such as used in the manufacture of cocoa butters or as cooking or frying pan release agents tend to degrade the lecithin and produce off-flavors. Phosphatides enzymatically treated in accordance with this invention appear to possess greater thermal stability than those prouced under the traditional phosphatide manufacture. The treated phosphatides also appear to possess an enhanced low temperature stability. The enzymatic treatment alters the polysaccharide components without enzymatically altering the phosphatide. Rheological changes imparted to the phosphatide composition, as a whole, by enzymatic modification of the indigenous carbohydrates therein is believed to be responsible for these unique functional and physical improvements.

EXAMPLE 1

This example illustrates the fluidization of a dry, non-fluid lecithin (65 A.I.)product. In a three-neck 100 ml. round bottom flask equipped with an agitator, vacuum drying means and a temperature controlled bath, 37.5 g of a dehydrated lecithin (obtained from hexane/alcohol azeotropic extracted oil—Example 1 of U.S. Pat. No. 4,221,731 by Short et al.) was enzymatically converted into a fluid lecithin product. The enzymes (8.9 mg invertase and 8.2 mg glucose oxidase) were dissolved in distilled water (10 ml.) and then added with moderate agitation to the dehydrated lecithin (60° C.). The lecithin and enzyme mixture (pH 5.1) was adjusted to 50% by weight lecithin solids concentration by adding 27 ml. of distilled water to the flask. The mixture (pH 5.1) was then digested for 30 minutes at 60° C. The enzymatically digested lecithin composition was dried at 90° C. under 28 in. vacuum (mercury) for one hour. The dehydrated enzymatically treated lecithin still remained fluid, without any evidence of phase separation, after 10 months.

A control sample processed under identical conditions except for the enzymatic treatment set up into a solid mass within 40 minutes.

EXAMPLE 2

In this example 815.7 g of a hexane/ethanol azeotropic extracted crude oil (Example 1 of U.S. Pat. No. 4,221,731) was degummed with 4.1 ml. of an aqueous divalent metal ion solution (4.3% calcium chloride and 6.2% magnesium chloride on a weight basis) and 12 ml. of water. The hydrated lecithin product was recovered from the crude oil by centrifugation (2170 g's for 15 minutes) to yield a low A.I. (@ 31%) lecithin product. Ninety-one (91) grams of the degummed lecithin product containing 59 g lecithin (dry substance basis) were placed into a three-neck flask equipped with a stirrer, thermometer and a vacuum. An enzyme preparation was separately prepared by dissolving 2.2 mg glucose oxidase and 3.9 mg invertase in a sufficient amount of water to adjust the lecithin solids level (d.s.b) to 50% by weight. The enzyme preparation was then added to the flask. The digestion (pH 6.9) was conducted with continuous stirring at 45° C. for 30 minutes. The digested lecithin product was then heated to 105° C. and vacuum-dried (28" Hg vacuum) to less than a 0.5% by weight moisture content.

For comparative purposes, a control sample was processed under identical conditions except that the enzymatic treatment with glucose oxidase and invertase was omitted from the control test. The divalent metal concentration (based upon a 65% A.I. lecithin) for the control sample was 0.61% and 0.58% for the digested sample.

Within 12 hours the control sample solidified while the digested lecithin product still remained fluid after one week of storage. It is anticipated that the stability of the enzymatically treated fluid lecithin product will be comparable to the fluidized product of Example 1. As illustrated by this example, the enzymatic treatment converts low A.I. lecithin products into a fluidized, shelf-stable, non-separable, lecithin product. In contrast, the undigested lecithin product was unstable, as evidenced by its solidification within 12 hours after its preparation. Since the low A.I. lecithins are especially prone to solidification or separation, this example further illustrates the fluidization of a lecithin product which was heretofore considered unsuited for conversion into a shelf-stable lecithin product. Crude oils extracted from vegetable seed products with polar solvent containing systems (e.g. alcohol containing defatting solvents) will typically yield a degummed lecithin product containing a higher carbohydrate concentration that normally obtained by conventional hexane extracted crude oils. The presence of these carbohydrate excesses accentuates the fluidity problem encountered in the manufacture of lecithin products obtained from crude oils extracted via such polar solvent containing systems.

What is claimed is:

1. A method for converting phosphatide compositions which contain O-glycosyl compounds into a fluid phosphatide composition, said method consisting essentially of enzymatically treating the phosphatide composition with an effective amount of O-glycosyl hydrolase to hydrolyze the O-glycosyl compound within said phosphatide composition and thereby improve upon the fluidity characteristics of said phosphatide composition, and recovering the fluid phosphatide composition therefrom.

2. The method according to claim 1 wherein the enzymatic treatment of the phosphatide with hydrolase is combined with an effective amount of a supplemental enzyme to convert the hydrolyzed O-glycosyl compound into hydrogen peroxide.

3. The method according to claim 2 wherein the supplemental enzyme consists essentially of glucose oxidase.

4. The method according to claim 1 wherein the hydrolyase comprises a glucosidase.

5. The method according to claim 1 wherein the hydrolase consists essentially of beta-fructofuranosidase.

6. The method according to claim 5 wherein the phosphatide is enzymatically treated with the beta-fructofuranosidase in combination with glucose oxidase.

7. The method according to claim 6 wherein the phosphatide is derived from alcohol/hexane extracted crude oil.

8. The phosphatide composition prepared in accordance with the method of claim 1.

9. The phosphatide composition prepared in accordance with the method of claim 6.

10. The phosphatide composition prepared in accordance with the method of claim 7.

* * * * *